United States Patent [19]
Busse et al.

[11] Patent Number: 5,359,760
[45] Date of Patent: Nov. 1, 1994

[54] METHOD OF MANUFACTURE OF MULTIPLE-ELEMENT PIEZOELECTRIC TRANSDUCER

[75] Inventors: Lawrence J. Busse, Littleton, Colo.; Jeffry W. Stevenson; Wayne Huebner, both of Rolla, Mo.

[73] Assignee: The Curators of the University of Missouri on behalf of the University of Missouri-Rolla, Columbia, Mo.

[21] Appl. No.: 46,965

[22] Filed: Apr. 16, 1993

[51] Int. Cl.$^5$ ............................................. H04R 17/00
[52] U.S. Cl. ................................. 29/25.35; 310/358; 310/800
[58] Field of Search ............... 29/25.35; 310/334–337, 310/357, 358, 800; 264/63

[56] References Cited

U.S. PATENT DOCUMENTS

| | | |
|---|---|---|
| 4,353,958 | 10/1982 | Kita et al. |
| 4,359,271 | 11/1982 | Mihara . |
| 4,514,247 | 4/1985 | Zola . |
| 4,518,889 | 5/1985 | 'T Hoen . |
| 4,564,980 | 1/1986 | Diepers . |
| 4,572,981 | 2/1986 | Zola . |
| 4,717,851 | 1/1988 | Fenner et al. |
| 4,747,192 | 5/1988 | Rokurota ............... 29/25.35 |
| 4,939,826 | 7/1990 | Shoup . |
| 4,977,655 | 12/1990 | Martinelli . |
| 5,153,859 | 10/1992 | Chatigny et al. |

OTHER PUBLICATIONS

A Precision Tape Casting Machine for Fabricating Thin Ceramic Tapes, R. B. Runk and M. J. Andrejco, Western Electric Co., Engineering Research Center, Princeton, N.J., Ceramic Bulletin, vol. 54, No. 2 (1975).
Tape Casting: The Basic Process for Meeting the Needs of the Electronics Industry, Richard E. Mistler, Keramos Industries, Inc., Morrisville, Pa. 19067, Ceramic Bulletin, vol. 69, No. 6, 1990.
Tape Casting, Richard E. Mistler, Keramos Industries, Inc., reprinted from Engineered Materials Handbook, The Materials Information Society, vol. 4: Ceramics and Glasses.
Processing Parameters and Electric Properties of Doctor-Bladed Ferroelectric Ceramics, Chandler Wentworth and George W. Taylor, RCA Laboratories, Princeton, N.J., Ceramic Bulletin, vol. 46, No. 12 (1967).

Primary Examiner—Carl E. Hall
Attorney, Agent, or Firm—Michael M. de Angeli

[57] ABSTRACT

An improved method for fabrication of a multiple-element piezoelectric transducer and the transducer produced thereby. A green precursor tape is produced by doctor-blade tape-casting of a slurry containing lead zirconate-titanate (PZT) powder. After drying, individual strips of the tape are stacked between flat plates of previously sintered PZT, and sintered to form PZT strips; Pb from the previously sintered PZT plates makes up any Pb lost from the surfaces of the tape strips during sintering. The PZT strips are stacked interposed by layers of a thermoplastic polymer, and heated to a temperature above the melting point of the polymer, forming a laminate block. This block is then sliced perpendicular to the plane of the layers, forming slabs of alternate PZT and polymer layers; the slabs are then sliced perpendicular to the first slicing planes, forming strips of alternating PZT and polymer material. Electrodes are then added to complete the transducer assembly.

28 Claims, 2 Drawing Sheets

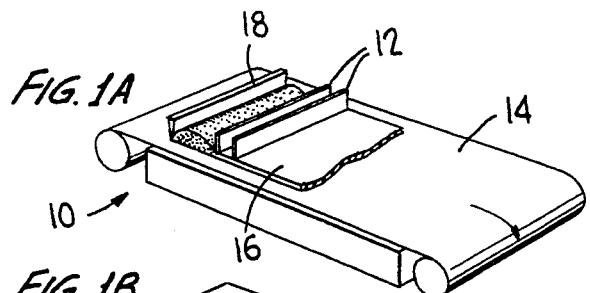

FIG. 1A

FIG. 2A
PREPARE SLURRY; FORM GREEN PRECURSOR TAPE USING DOUBLE DOCTOR BLADE TAPE CASTING; DRY

FIG. 1B

FIG. 2B
CUT PRECURSOR TAPE INTO STRIPS, STACK STRIPS WITH PZT SPACERS, SINTER

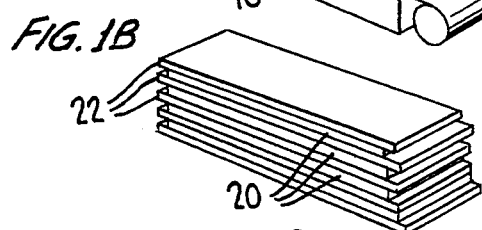

FIG. 1C

FIG. 2C
PREPARE POLYMER TAPE USING DOUBLE DOCTOR BLADE TAPE CASTING

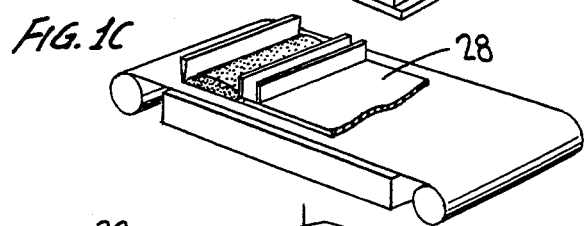

FIG. 1D

FIG. 2D
STACK SINTERED PZT PLATES WITH POLYMER; BAKE UNDER COMPRESSION AND VACUUM

FIG. 1E

FIG. 2E
SLIT ALONG CUTTING PLANES PERPENDICULAR TO PLANE OF LAYERS

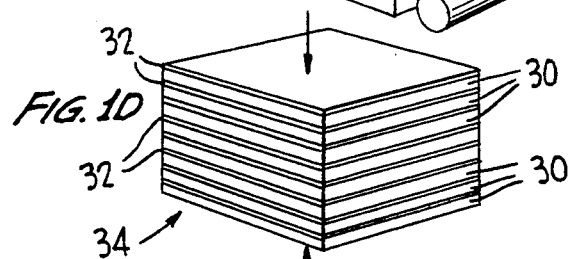

FIG. 1F

FIG. 2F
SLIT SLABS ALONG CUTTING PLANES PERPENDICULAR TO FIRST CUTTING PLANES

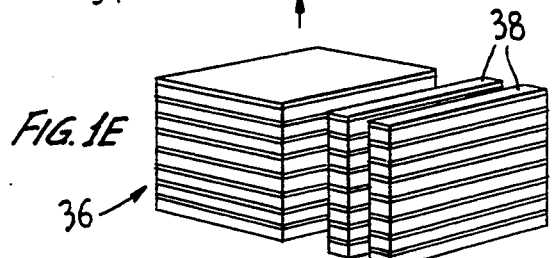

FIG. 1G

FIG. 2G
APPLY ELECTRODES AND CONDUCTORS

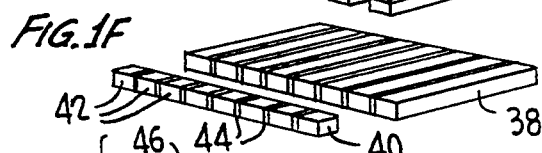

FIG. 1H

FIG. 2H
ADD IMPEDANCE MATCHING LAYERS AND BACKING LAYER

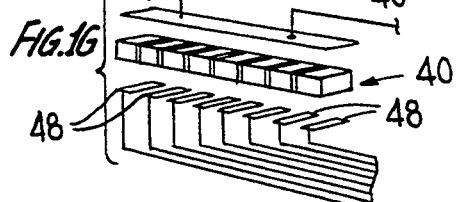

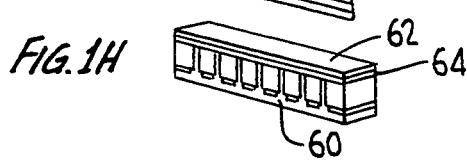

METHOD OF MANUFACTURE OF MULTIPLE-ELEMENT PIEZOELECTRIC TRANSDUCER

GOVERNMENT INTEREST

This invention was made with government support under Contract No. HL44230 awarded by the National Institutes of Health. The government has certain rights in the invention.

BACKGROUND OF THE INVENTION

1. Field of the Invention

This invention relates to methods of manufacture of multiple-element piezoelectric transducers, for example, suitable for ultrasonic imaging applications in medicine and elsewhere.

2. Description of the Prior Art

Multiple-element piezoelectric transducers are known for use in several applications, in particular for nondestructive imaging of the interior of structures. For example, endoscopic imaging probes have been proposed for numerous medical applications. In many such imaging applications, it is desired to reduce the size of the individual piezoelectric elements as much as possible, to allow operation at higher frequencies and thereby provide increased resolution in the image.

Most present day piezoelectric transducers are fabricated of lead zirconate-titanate (PZT) ceramic material. The PZT material is commonly prepared from a PZT powder produced by mixing individual oxides (PbO, $TiO_2$, $ZrO_2$, plus small quantities of modifiers) and "calcining" the mixture. The calcination step is accomplished by heating the mixture to a high enough temperature (e.g., 800°–900° C.) to cause the constituent oxides to react to form single phase PZT in solid solution. The exact proportions of the constituent powders are varied in accordance with the specific properties desired in the PZT material being prepared. The calcined PZT is then ground to a fine powder, e.g., by conventional ball milling techniques. Dense blocks of PZT ceramic in desired shapes can then be formed by compacting the PZT powder in a die and then "sintering" the resultant "green" block at a suitable temperature (typically 1200°–1300° C.). Hot pressing, in which the PZT powder is subjected to external pressure during sintering, is also an effective way to produce blocks of PZT ceramic.

During the sintering process, some of the Pb content tends to be driven off, particularly from the surface of the pellet, with adverse effects on the properties of the ceramic; accordingly, it is known to place a quantity of Pb-containing material, such as $PbZrO_3$, in the sintering furnace during the sintering step. Alternatively, the surface of the sintered block may be removed and discarded, after which the internal material is sliced into thin plates which are then lapped flat to form PZT plates for further processing, such as dicing into small individual elements for assembly into multiple-element arrays.

U.S. Pat. Nos. 4,514,247 and 4,572,981 to Zola disclose one proposed alternative in fabrication of multiple-element PZT transducer arrays. A single plate of PZT material prepared generally as above is diced into smaller slabs, which are then stacked interposed with layers of a passive material, such as glass, paper, phenolic resin, silicone rubber, or another ceramic material. The PZT slabs may be bonded to the layers of passive material using epoxy cement. The laminate block thus formed is then sliced perpendicular to the plane of the layers, resulting in plates comprising alternating strips of PZT and the passive material. These plates are then stacked, again interposed with layers of the passive material, and this assembly is sliced perpendicular to the strips, to yield one or more planar members in which PZT elements are surrounded by passive material. Single or separately-addressable electrodes are then applied to the opposed planar ends of the planar members.

Production of multiple-element transducer arrays according to the Zola method requires that the PZT plates be lapped to a desired thickness. As the lapping process requires a minimum strength, PZT elements manufactured according to the Zola process have an undesirably large minimum thickness. Zola's method also requires that individual members of the passive material be separately bonded to the PZT elements, which is a time-consuming and complex process. Zola also fails to teach an efficient method of connection of individual conductors to the individual PZT elements.

Other methods of fabrication of multiple-element arrays require multiple fine pitch dicing steps to form finely-divided PZT elements for subsequent assembly. Assembly of such small elements is very difficult. Moreover, the PZT material must be relatively fine grained (grain size $\leq 2$ microns) to withstand the abrasive cutting technique employed in the dicing process. Relatively coarsely-grained PZT material (grain sizes $\geq 3-5$ microns) exhibits higher piezoelectric sensitivity. Accordingly, At would be desirable to avoid dicing insofar as possible in the preparation of multiple-element PZT arrays, to allow use of the preferable coarsely-grained material.

A technique known as "tape-casting" is commonly employed for manufacture of "green" precursor tapes formed of materials which when sintered form a desired ceramic material. In tape-casting, a slurry is prepared including powders of the materials of the ceramic of interest, together with organic solvents and binders. A pool of the slurry, termed the "slip", is poured onto a moving substrate, between a stationary dam and one or two "doctor blades" extending parallel to the dam and spaced vertically from the moving substrate. As the substrate is pulled beneath the doctor blades, the thickness of the green precursor tape is precisely controlled by the spacing of the doctor blades from the substrate. Equivalently, tape casting can be performed by pulling one or a pair of mobile doctor blades across a stationary substrate. The green precursor is then dried and sintered to form the ceramic material. See, e.g., Runk and Andrejco, "A Precision Tape Casting Machine for Fabricating Thin Ceramic Tapes", *Ceramic Bulletin*, 54, No. 2, 199–200 (1975); Mistler, "Tape Casting: The Basic Process for Meeting the Needs of the Electronics Industry", *Ceramic Bulletin*, 69, No. 6, 1022–1026 (1990); Mistler, "Tape Casting", in *Engineered Materials Handbook*, 4, 161–165, (1992). See also U.S. Pat. No. 4,353,958 to Kita et al. Moreover, Wentworth and Taylor, in "Processing Parameters and Electric Properties of Doctor-Bladed Ferroelectric Ceramics", *Ceramic Bulletin*, 46, No. 12, 1186–1193, (1967), suggest that the properties of $Pb(ZrSnTi)O_3$ ferroelectric ceramics prepared using doctor-bladed tape-casting techniques as above may be improved by disposing a source of Pb-containing material in the sintering furnace during the sintering step. More specifically, according to this technique, a green precursor tape is cut into strips and placed between Pb-rich "setter" members spaced about 2 mils from the surface of the green precursor strips. During sintering the presence of a Pb-containing setter increases the local Pb activity, thus minimizing Pb loss from the green tape and maintaining the proper ceramic composition.

Other references generally pertinent to the present invention include U.S. Pat. No. 4,939,826 to Shoup and U.S. Pat. No. 4,564,980 to Diepers, disclosing methods of manufacture of particular transducers; U.S. Pat. No. 4,977,655 to Martinelli, disclosing a method for mounting two transducers on a single catheter, for medical imaging purposes; U.S. Pat. No. 4,518,889 to 'T Hoen teaching an apodized transducer, that is, one having a particular asymmetric response; and U.S. Pat. No. 4,717,851 to Fenner et al, disclosing particular acoustic impedance matching layers for ultrasonic transducers.

OBJECTS OF THE INVENTION

It is therefore an object of the invention to provide an improved method for the production of flat ceramic members which avoids extensive sawing or lapping steps practiced in the prior art.

It is therefore a further object of the invention to provide an improved method for the production of multiple-element piezoelectric transducers in which the grain size of the piezoelectric material is not limited by the processing steps employed.

It is still a further object of the invention to provide a simplified method for the production of multiple-element piezoelectric transducers.

It is yet a further object of the invention to provide an improved method for the production of multiple-element piezoelectric transducers including a simplified method for connection of conductors to the piezoelectric elements of the transducer.

It is a further object of the invention to provide an improved multiple-element piezoelectric transducer.

SUMMARY OF THE INVENTION

The present invention meets the needs of the art and objects of the invention mentioned above, as well as others apparent from the following discussion, by provision of an improved method for fabrication of a multiple-element transducer and the transducer produced thereby. According to the invention, a green precursor tape is produced by doctor-blade tape-casting of a slurry containing PZT powder. The precursor tape is dried. Individual strips of the green tape are stacked between flat spacers of previously sintered PZT. The stacked strips are sintered to form PZT plates. The previously-sintered PZT spacers maintain a high degree of local Pb activity to minimize Pb loss from the surfaces of the tape strips during sintering.

The PZT plates are then separated from the previously sintered PZT spacers, and are stacked interposed by layers of a thermoplastic polymer. This stack is then heated while under compression, and while a vacuum is applied, to a temperature above the melting point of the polymer, forming a laminate block. This block is then sliced perpendicular to the plane of the layers, forming slabs of alternate PZT and polymer layers; the slabs are then sliced perpendicular to the first slicing planes, forming elongate members of alternating layers of PZT and the polymer material.

A front electrode is then formed on one side of each of the elongate members, and a series of rear electrodes is applied to the opposite side of each of the elongate members using an anisotropically-conductive adhesive. The lateral pitch of the electrodes may be such that several PZT elements are connected to a single electrode. One or more layers of a impedance-matching materials are then provided, together with a backing layer, forming a complete transducer head assembly.

BRIEF DESCRIPTION OF THE DRAWINGS

The invention will be better understood if reference is made to the accompanying drawings, wherein:

FIG. 1, including FIGS. 1(a)–1(h), comprises a sequence of perspective schematic views illustrating the principal stages in fabrication of a multiple-element transducer according to the invention;

FIG. 2, including FIGS. 2(a)–2(h), comprises a corresponding sequence of verbal descriptions of the principal stages in fabrication of a multiple-element transducer according to the invention;

DESCRIPTION OF THE PREFERRED EMBODIMENTS

Figure 3:
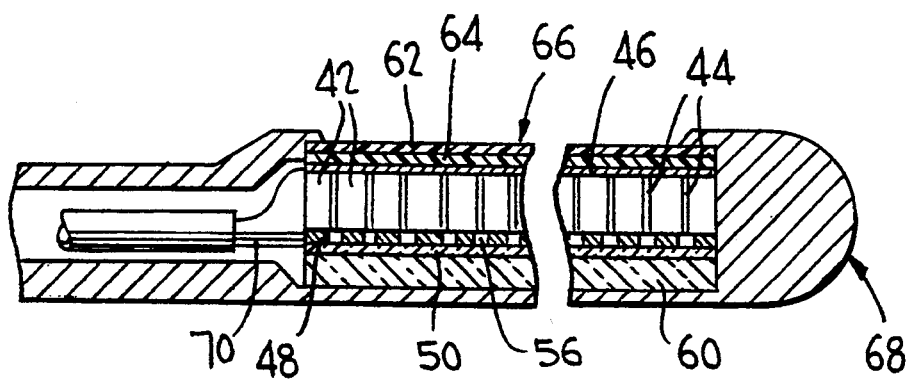
FIG. 3 is a cross-sectional view of the distal tip of an ultrasonic probe comprising a multiple-element piezoelectric transducer according to the invention.

As indicated above, FIGS. 1 and 2 provide corresponding schematic illustrations and verbal explanations of the stages in fabrication of multiple-element piezoelectric transducers according to the invention. FIGS. 1(a) and 2(a) describe the formation of a green precursor tape. In the preferred embodiment, the desired piezoelectric ceramic material to be prepared is lead zirconate-titanate (PZT). In this case, a PZT powder is prepared by mixing and calcining PbO, $TiO_2$, $ZrO_2$, and small quantities of modifier oxides in the appropriate proportions. The properties of the PZT can be varied by suitably varying the ratios of the constituent oxides. The calcined PZT is then processed to form a PZT powder, e.g., by ball milling. In accordance with the teachings of the ceramic tape-casting art discussed above, the PZT powder is further mixed with known organic solvents, plasticizers, binders and the like to form a slurry. The slurry is then poured onto a substrate 14 moving with respect to a pair of double doctor blades 12 in a generally conventional tape casting system 10, the slurry thus forming the "slip" of the tape-casting process. The slip is confined between a dam 18 and the doctor blades 12, so that as the substrate 14 passes slowly beneath the doctor blades 12, a green precursor tape 16 is formed, the tape 16 being of very consistent thickness. The green precursor tape 16 is then dried; typically air-drying is sufficient.

According to one aspect of the invention, and as depicted in FIGS. 1(b) and 2(b), the dried green precursor tape 16 is then cut into strips 20, which are stacked, interposed with spacers 22 of previously sintered PZT material, after which the stack is sintered, such that the green precursor strips 20 are converted to sintered ceramic PZT plates. There are several advantages to thus sintering the green precursor strips 20 while interposed in a stack with previously sintered PZT spacers 22. As noted, the previously sintered PZT spacers 22 maintain a high local Pb activity which minimizes Pb loss from the green precursor strips 20 during sintering. Preferably, the previously sintered PZT spacers 22 are lapped flat, form the uppermost and lowermost elements in the stack, and are in direct contact with the green precursor strips 20, to ensure that the sintered PZT ceramic plates formed upon sintering the green precursor strips 20 are flat, eliminating any necessity of lapping the PZT ceramic plates.

It will be appreciated that according to this aspect of the invention, the green precursor strips are prepared as a thin (e.g., 100 micron) tape 16, which is subsequently cut into strips and fired. Since such a thin tape has a relatively high ratio of surface area to volume, the problem of Pb loss during sintering will be particularly acute if not avoided. Further, the thin PZT plates resulting from sintering of such a thin tape are not strong enough to be lapped, whereby a Pb-depleted surface layer might be removed. According to the invention, Pb-containing previously sintered PZT spacers 22 are provided in direct contact with the green precursor strips 20 during the sintering step. The PZT spacers 22 separate the green precursor strips 20, minimize Pb loss, and constrain the PZT plates formed upon sintering of the strips 20 to remain flat, such that lapping of the PZT plates is unnecessary. As is well known, the green precursor strips 20 shrink substantially during sintering, such that the PZT plates formed do not tend to adhere to the previously sintered PZT spacers 22.

The sintering step may be carried out by placing the stacked green precursor strips 20 and previously sintered PZT spacers 22 in an alumina crucible, placing the crucible in a sintering furnace having an oxidizing atmosphere, and gradually raising the temperature to on the order of 500° C. to volatilize and remove the organic binders, plasticizers, and the like used to provide a workable slurry. The temperature may then be raised to substantially 1250° C. and maintained for on the order of 0.5 hour, to densify and solidify the green precursor material, forming solid PZT plates between the previously sintered PZT spacers 22. It may further be preferable to place a quantity of $PbZrO_3$ powder in the sintering crucible, to ensure sufficient Pb is available during the sintering step. The resulting products are thin (as little as 15 microns) plates of PZT having desired relatively coarse grain sizes of 5–10 microns. According to this aspect of the method of the invention, these products are obtained without sawing or lapping steps; stated differently, according to the invention, PZT plates may be produced having piezoelectric properties which are not compromised by the mechanical steps necessary for their production.

The same process may be employed for preparing plates of other ceramic materials, such as modified lead titanates, e.g., $(Pb,Ca)TiO_3$ and $(Pb,Sm)TiO_3$, lead metaniobate, or barium titanate, which are used for other purposes. Again, the method of the invention allows preparation of ceramic members of desired properties free from constraints imposed by other preparation methods involving extensive sawing or lapping operations.

FIGS. 1(d)–(h) and 2(d)–(h) illustrate the principal steps performed in fabrication of multiple-element piezoelectric transducers using PZT plates produced using the methods described above. At the step shown by FIGS. 1(d) and 2(d), the sintered PZT plates 30 are assembled in a stack 34, the PZT plates 30 being interposed with layers 32 of a thermoplastic polymer, such as polyvinyl butyral (PVB) or polyvinyl formal (PVF). Manufacture of the transducer produced according to the method of the invention is significantly simplified if the number of total PZT elements in a single row of the complete transducer is equal to the number of PZT plates 30 in the stack 34. Several hundred alternate layers 32 of the polymer and plates 30 of PZT material may therefore be provided in stack 34.

As indicated by FIGS. 1(c) and 2(c), the PVB or PVF material may be prepared as a sheet 28, using a tape-casting process as discussed generally above, but this is not a limitation on the invention. Tape-casting the polymer allows selection from a wide range of polymer thicknesses, and allows convenient introduction of plasticizers and fillers to tailor the acoustic impedance and attenuative properties of the polymer sheets.

The stack 34 of alternating PZT plates 30 and polymer layers 32 is then placed in a furnace and baked to reach a temperature at least equal to the melting point of the polymer material (for example, 160° C. for PVB or 210° C. for PVF), such that the polymer when cooled bonds the PZT plates 30 into a solid block 36. As indicated, axial compression may be applied during the baking step, and this step may be carried out under vacuum, to improve the properties of the block 36. Thus, the polymer both provides a passive material separating the PZT plates and bonds the PZT plates into a unitary block. The block 36 having plates 30 of PZT interspersed with passive polymer layers 32 is referred to in the art as a "2—2 composite". If prepared as indicated, no voids will exist between the plates 30 of the PZT ceramic material.

As depicted in FIGS. 1(e) and (f) and 2(e) and (f), the block 36 is then slit into elongated laminate members 40 comprising alternating PZT elements 42 and polymer layers 44, in two slitting steps. The block 36 is first slit along a number of parallel first cutting planes perpendicular to the planes of the plates of PZT material and polymer (FIG. 1(e)), forming slabs 38 comprising alternate layers of the PZT and polymer materials. The slabs 38 are then slit along a number of parallel second cutting planes perpendicular to the first cutting planes and to the planes of the plates of PZT material and polymer (FIG. 1(f)), forming elongated laminate members 40, of generally square cross-section, having alternate PZT elements 42 spaced by layers 44 of polymer extending along their length.

As illustrated by FIGS. 1(g) and 2(g), front and rear electrodes are then applied to each elongated laminate member 40 to fabricate a multiple-element transducer. Several possible embodiments of the structure of the electrodes are detailed below in connection with FIGS. 3 and 4. Typically, the front electrode 46 may comprise a continuous metallized surface applied by electroless plating, sputtering, or vapor deposition directly to one side of the elongated laminated member 40. Individual rear electrodes 48 are connected to the PZT elements 42. The transducer is completed by impedance matching layers 62 and 64 and a backing layer 60, as illustrated in FIGS. 1(h) and 2(h).

The rear electrodes 48 may comprise individual traces printed on a flex circuit element 50 (i.e., individual conductors formed as part of a printed circuit on a flexible substrate) at the same spacing as the PZT elements 42 and bonded thereto by a film 56 of a commercially available anisotropically conductive adhesive material, e.g., "Z-Axis Adhesive Film" available as Part No. 5303R from the 3M Corporation. See FIG. 3. This method of connecting the electrodes 48 to the PZT elements 42 requires that the pitch (i.e., the spacing) of the electrodes 48 and PZT elements 42 be equal over the length of the transducer assembly.

Figure 4:
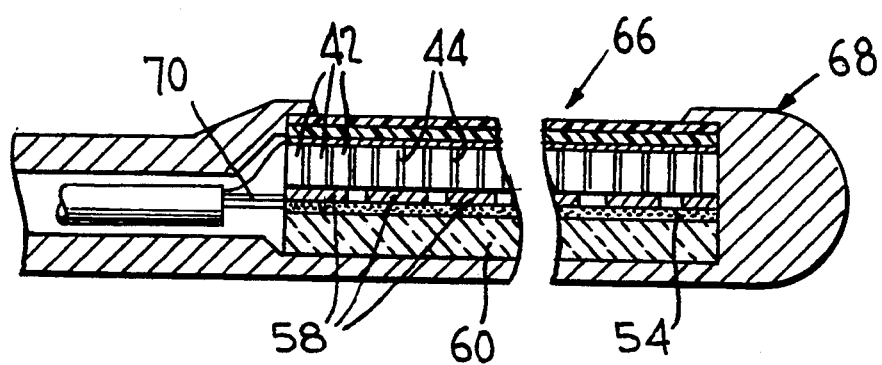
FIG. 4 is a view corresponding to FIG. 3, illustrating a somewhat different embodiment of the invention.

In an alternative embodiment of the invention shown in FIG. 4, the PZT elements 42 may be formed at substantially finer pitch than the rear electrodes 58, such that each electrode 58 is connected (using the same conductive adhesive) to several, typically two or three, of the PZT elements 42. Connecting each electrode 58 to several of the PZT elements 42 renders the relative pitch thereof less critical. FIG. 4 also illustrates an alternative method of forming the electrodes 58, namely by printing directly onto a ceramic substrate 54. The electrodes 58 and the conductors 70 to which the electrodes are connected might also be printed directly onto a backing layer 60 typically applied to protect the rear surface of the laminate member 40. Backing layer 60 is typically also provided in the embodiment of FIG. 3, as shown.

As further illustrated in FIGS. 3 and 4, a multiple-element transducer 66 according to the invention is completed by one or more layers 62, 64 of acoustic impedance matching materials. Layers 62, 64 are provided in order to match the very high acoustic impedance of the hard ceramic elements 42 to the material with which the transducer 66 is intended to be used. Where the transducer 66 is to be used for medical imaging purposes, such that the transducer 66 will function to transmit ultrasonic energy into body tissues and detect reflection of energy from internal structures and the like, suitable impedance matching layers 62 and 64 may be formed of glass and epoxy, respectively, as generally known in the art. As noted above, a backing layer 60 is commonly provided as well; a suitable material is tungsten-loaded epoxy, again as generally known in the art.

A complete transducer 66 may include a single elongate laminate assembly as described above, for emitting energy into a structure to be examined and detecting energy reflected therefrom, may comprise several such assemblies arranged in line with one another, providing a longer one-dimensional array of transducer elements, or may comprise a number of such assemblies in a two-dimensional array. The transducer 66 may be conveniently mounted at the distal tip of a probe 68, for being maneuvered into contact with tissues or other structures to be imaged or otherwise examined using energy emitted by the transducer 66. Conductors 70 connected to the electrodes 46, 48 pass through a lumen extending along the axis of probe 68 and are connected to excitation and analysis circuitry, for supplying energy transmitted into the structure to be examined and analysis of the reflected energy, all generally as known in the art. Typically pulses of high-frequency energy will be applied between the front electrode 46 and selected ones of the rear electrodes 48, to cause the corresponding PZT elements 42 to transmit bursts of ultrasonic energy into the structure to be examined; electrical signals emitted by each of the PZT elements 42 responsive to detection of reflected energy are then transmitted by conductors 70 to data analysis and imaging equipment, again generally as known in the art.

While a preferred embodiment of the invention has been disclosed in detail, this exemplary disclosure should not be considered to limit the invention, which is limited only by the following claims.

What is claimed is:

1. A method for manufacture of a plurality of flat plates of lead zirconate-titanate (PZT) piezoelectric material, comprising the steps of:

preparing a slurry comprising PZT powder in a liquid binder;

forming a green precursor tape by tape-casting said slurry;

allowing said green precursor tape to dry;

cutting said green precursor tape into strips;

stacking said strips of green precursor tape, said strips being interspersed by and in direct contact with flat spacer members comprising sintered PZT;

sintering said stacked strips of precursor tape and PZT spacer members, forming flat PZT plate members; and removing said spacer members from said flat PZT plate members.

2. The method of claim 1, wherein said sintering step is performed in a furnace, and a quantity of Pb-containing material is placed in said furnace during said sintering step.

3. The method of claim 2, wherein said Pb-containing material is $PbZrO_3$.

4. The method of claim 2, wherein the temperature within said furnace during said sintering step is gradually increased from room temperature to approximately 500° C., followed by maintenance of the temperature within said furnace at approximately 1250° C. for at least on the order of 0.5 hours.

5. A method for manufacture of a multiple-element piezoelectric transducer, comprising the steps of:

preparing a slurry comprising PZT powder in a liquid binder;

forming a green precursor tape by tape-casting said slurry;

allowing said green precursor tape to dry;

cutting said green precursor tape into strips;

stacking said strips of green precursor tape interspersed with flat spacer members comprising sintered lead zirconate-titanate (PZT);

sintering said stacked strips of precursor tape, forming flat PZT plate members;

separating the sintered plate members from the spacer members;

stacking a plurality of said PZT plate members interspersed with thermoplastic polymer members;

heating said stack of PZT and polymer members, forming a unitary multiple-layer laminate of PZT layers spaced from and bonded to one another by polymer layers;

slicing said laminate along first cutting planes substantially perpendicular to the planes of said layers of PZT and polymer, forming substantially flat slab members;

slicing said slab members along second cutting planes perpendicular to both said first cutting planes and the planes of said layers of PZT and polymer, forming elongated laminate members comprising a plurality of layers of PZT spaced by layers of polymer; and applying conductive electrodes to edges of the PZT layers exposed on opposite sides of each of the elongated laminate members.

6. The method of claim 5, wherein said polymer material is polyvinyl butyral or polyvinyl formal.

7. The method of claim 5, comprising the further step of compressing the stacked polymer and sintered plate members during said heating step.

8. The method of claim 5, comprising the further step of applying a vacuum to the stacked polymer and sintered plate members during said heating step.

9. The method of claim 5, comprising the further step of preparing said layers of polymer by tape-casting.

10. The method of claim 5, wherein said step of applying conductive electrodes to exposed edges of the PZT layers on opposite sides of each elongated laminate member is performed by applying at least one metallized surface to a first front elongated surface of the elongated laminate member, and applying a series of individual electrodes to an opposite rear elongated surface of the elongated laminate member, and connecting conductors to said metallized surface and to said series of individual electrodes.

11. The method of claim 10, wherein said step of applying a metallized surface is performed by electroless plating, by sputtering, or by vapor deposition.

12. The method of claim 10, wherein said step of applying a series of individual electrodes is performed by bonding individual traces on a flex circuit member to exposed edges of the PZT layers using an anisotropically conductive adhesive material.

13. The method of claim 10, wherein said series of individual electrodes are each substantially wider than the corresponding thickness of the PZT members to which the electrodes are applied such that each electrode is connected to the edges of several PZT members.

14. The method of claim 10, wherein said step of applying a series of individual electrodes is performed by bonding individual conductors formed on a ceramic substrate to the exposed edges of the PZT layers, using an anisotropically conductive adhesive material.

15. A method for manufacture of a multiple-element piezoelectric transducer, comprising the steps of:
preparing a plurality of strips of a green precursor tape including PZT materials;
stacking said strips interspersed with flat spacer members formed of a previously-sintered Pb-rich ceramic material;
sintering said strips interspersed with said spacer members, to form a plurality of flat PZT plate members;
stacking said plurality of flat PZT plate members interspersed with thermoplastic polymer members;
heating said stack of PZT and polymer members, forming a unitary multiple-layer laminate of PZT layers spaced from and bonded to one another by polymer layers;
slicing said laminate along first cutting planes substantially perpendicular to the planes of said layers of PZT and polymers, forming substantially flat slab members;
slicing said slab members along second cutting planes perpendicular to both said first cutting plane and the planes of said layers of PZT and polymer, forming elongated laminate members comprising a plurality of layers of PZT spaced by layers of polymer; and
applying conductive electrodes to edges of the PZT layers exposed on opposite sides of each of the elongated laminate members.

16. The method of claim 15, wherein said polymer material is polyvinyl butyral or polyvinyl formal.

17. The method of claim 15, comprising the further step of compressing the stacked polymer and sintered plate members during said heating step.

18. The method of claim 15, comprising the further step of applying a vacuum to the stacked polymer and sintered plate members during said heating step.

19. The method of claim 15, comprising the further step of preparing said layers of polymer by tape-casting.

20. The method of claim 15, wherein said step of applying conductive electrodes to exposed edges of the PZT layers on opposite sides of each of the elongated laminate members is performed by applying a metallized surface to a first front elongated surface of each elongated laminate member, and applying a series of individual electrodes to an opposite rear elongated surface of the elongated laminate member, and providing connections to said metallized surface and to said series of individual electrodes.

21. The method of claim 20, wherein said step of applying a metallized surface is performed by electroless plating, by sputtering, or by vapor deposition.

22. The method of claim 20, wherein said step of applying a series of individual electrodes is performed by bonding individual traces on a flex circuit member to exposed edges of the PZT layers, using an anisotropically conductive adhesive material.

23. The method of claim 20, wherein said series of individual electrodes are each substantially wider than the corresponding thickness of the PZT members to which the electrodes are bonded, such that each electrode is bonded to the edges of several PZT members.

24. The method of claim 20, wherein said step of applying a series of individual electrodes is performed by bonding individual conductors formed on a substrate to the exposed edges of the PZT layers, using an anisotropically conductive adhesive material.

25. A method for manufacture of a plurality of flat plates of a desired ceramic material, comprising the steps of:
preparing a slurry comprising the desired ceramic material in powder form in a liquid binder;
forming a green precursor tape by tape-casting said slurry;
allowing said precursor tape to dry;
cutting said precursor tape into strips;
stacking said strips of precursor tape, said strips being interspersed by and in direct contact with flat spacer members formed of previously-sintered members of the desired ceramic material;
sintering said stacked strips of precursor tape and spacer members, forming flat plate members of said desired ceramic material; and
removing said spacer members from said flat plate members of said desired ceramic material.

26. The method of claim 25, wherein said desired ceramic material is selected from the group including lead zirconate-titanate, modified lead titanate, lead metaniobate, and barium titanate.

27. The method of claim 25, wherein said sintering step is performed by disposing said stacked strips of green precursor material and spacer members in a sintering furnace and operating said furnace to provide predetermined sintering conditions, and comprising the further step of providing an oxidizing atmosphere during said sintering step.

28. The method of claim 25, comprising the further step of providing a source of one or more of the elements of said desired ceramic material in said furnace during said sintering step.

* * * * *